United States Patent
Trentmann

[11] Patent Number: 5,935,563
[45] Date of Patent: Aug. 10, 1999

[54] SUBSTITUTED BENZYLIDENECYANOACETIC ACID ESTERS

[75] Inventor: Beate Trentmann, Manheim, Germany

[73] Assignee: BASF Aktiengesellschaft, Ludwigshafen, Germany

[21] Appl. No.: 09/051,898

[22] PCT Filed: Oct. 11, 1996

[86] PCT No.: PCT/EP96/04417

§ 371 Date: Apr. 15, 1998

§ 102(e) Date: Apr. 15, 1998

[87] PCT Pub. No.: WO97/15279

PCT Pub. Date: May 1, 1997

[30] Foreign Application Priority Data

Oct. 20, 1995 [DE] Germany .......................... 195 39 189

[51] Int. Cl.⁶ .......................... A61K 31/74; C07C 255/07
[52] U.S. Cl. .................. 424/78.03; 558/402; 558/416; 514/772; 514/772.1
[58] Field of Search .................. 558/402, 416; 424/78.03; 514/772.01

[56] References Cited

U.S. PATENT DOCUMENTS

| 3,462,475 | 8/1969 | Strobe . |
| 3,707,375 | 12/1972 | Reiichi et al. . |
| 4,284,621 | 8/1981 | Preuss et al. . |

FOREIGN PATENT DOCUMENTS

| 5 182 | 11/1979 | European Pat. Off. . |
| 757 036 | 3/1971 | France . |
| 1 443 920 | 11/1962 | Germany . |
| 1 087 902 | 8/1968 | Germany . |
| 28 16 819 | 10/1979 | Germany . |

OTHER PUBLICATIONS

Chem. Abst. Vol. 71, No. 23, Dec. 1969.

*Primary Examiner*—Johann Richter
*Assistant Examiner*—Ebenezer Sackey
*Attorney, Agent, or Firm*—Keil & Weinkauf

[57] ABSTRACT

A compound of the formula I

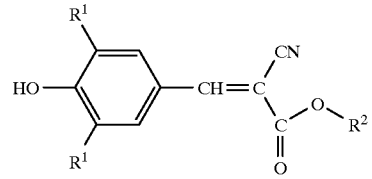

where
  $R^1$ is i-propyl, i-butyl or t-butyl,
  $R^2$ is alkyl with 6–14 carbon atoms,

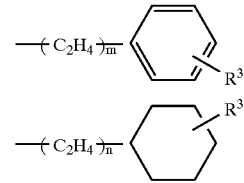

with $R^3$=H or $C_1$–$C_4$-alkyl and m, n=0 or 1.

4 Claims, No Drawings

SUBSTITUTED BENZYLIDENECYANOACETIC ACID ESTERS

This application is a 371 of PCI/EP96/04417 filed on Oct. 11, 1996.

The present invention relates to substituted benzylidenecyanoacetic esters of the formula I

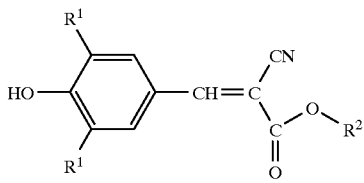

to the use thereof as sunscreen agents, to the use thereof in cosmetic products, and to cosmetic compositions comprising these compounds.

Sunscreen agents based on substituted benzylidenecyanoacetic esters are known.

BE 757 036 describes, inter alia, the compound

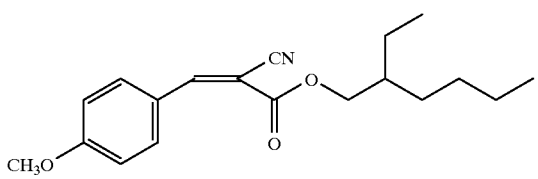

as light-sensitive photomaterial.

DE 10 87 902 describes condensates of benzaldehydes with compounds containing active methylene groups. Among many other compounds, mention is also made of condensates of 4-hydroxy-3,5-di-t-butylbenzaldehyde with diethyl malonate, cyanoacetic ester, malononitrile or malonic acid (page 1, second column, group VI). These compounds are described as suitable light stabilizers for films, sheets, fibers and filaments.

DE 28 16 819 describes substituted benzylidenecyanoacetic esters of the following structure as UV-A filters:

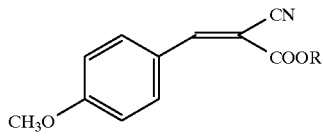

it being found that, with regard to possible substitution on the aromatic ring, para monosubstitution represents the optimum and, in turn, the methoxy radical confers optimal properties here. Concerning the radical R, it is found that compounds with R=n-hexyl, n-octyl, n-decyl, isononyl, and isodecyl are most suitable.

Since cosmetic sunscreen agents must, besides the photoproperties such as suitable absorption maximum, high specific extinction and photostability, have a number of other use properties such as good oil solubility, pH stability, oxidation stability, thermal stability, minimum intrinsic color and no intrinsic odor and, moreover, must also be toxicologically acceptable, it is an object of the present invention to optimize the previously disclosed products in respect of the abovementioned properties.

We have found that this object is achieved in that compounds of the formula I

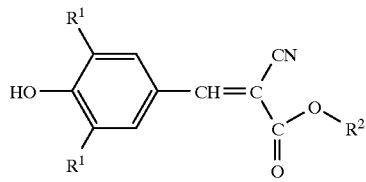

where
$R^1$ is i-propyl, i-butyl or t-butyl,
$R^2$ is alkyl with 6–14 carbon atoms,

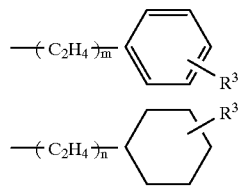

with $R^3$=H or $C_1$–$C_4$-alkyl and m, n=0 or 1, have better properties in respect of many of the abovementioned requirements, especially in respect of the photostability, than prior art compounds.

Particularly suitable sunscreen agents have been found to be compounds of the formula I where both $R^1$ radicals are tert-butyl and $R^2$ is a branched alkyl radical with 8–12 carbon atoms or —$C_2H_4$—$C_6H_5$ or

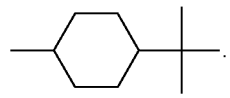

Moreover $R^2$ can be, for example, the radical

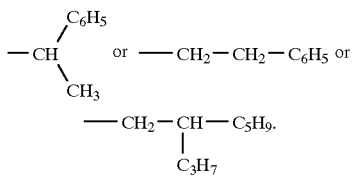

A particularly advantageous compound of the formula I is the one in which both $R^1$ radicals are tert-butyl and $R^2$ is

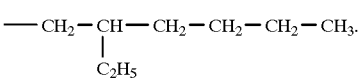

The compounds according to the invention can be prepared in a conventional way from the corresponding benzaldehydes and cyanoacetic esters in a Knoevenagel condensation (see, for example, Organikum, 1988 edition, page 459). The corresponding cyanoacetic esters were prepared by transesterification of a commercially obtainable cyanoacetic ester with the appropriate alcohol in a conventional way.

The compounds according to the invention are particularly suitable as light stabilizers for materials which are attacked by UV rays, for example filaments, fibers, sheets, films and other plastic moldings.

The compounds according to the invention are particularly suitable for protecting the human skin from UV rays. They can be used in a wide variety of cosmetic and medicinal products such as sun oils, sun creams, sun lotions, sun gels, lipsticks, skin creams, hair gels and non-greasy gels.

EXAMPLES

Example 1

2-Phenylethyl 3,5-di-tertiary-butyl-4-hydroxybenzylidenecyanoacetate 5.9 g of 3,5 di-tertiary-butyl-4-hydroxybenzaldehyde are [sic] dissolved in 50 ml of toluene.

4.7 g of 2-phenylethyl cyanoacetate, 0.1 g of piperidine and 0.25 g of acetic acid were heated to reflux. 0.4 g of $H_2O$ was removed azeotropically in 2 h. The mixture was cooled, washed with water and with sodium bicarbonate solution, dried and concentrated. The crude product was recrystallized.

Yield: 9.9 g (98%).

Example 2

2-Ethylhexyl 3,5-di-tertiary-butyl-4-hydroxybenzylidenecyanoacetate 28.1 g of 3,5-di-tertiary-butyl-4-hydroxybenzaldehyde were dissolved in 60 ml of toluene. 21.7 g of 2-ethylhexyl cyanoacetate, 0.27 g of piperidine and 0.67 g of acetic acid were added. The mixture was heated to reflux, and about 2 g of water were removed azeotropically. The clear solution was washed, dried and concentrated.

Yield: 46.2 g of pale yellow oil (93%).

Example 3

4-Tertiary-butylcyclohexyl 3,5-di-tertiary-butyl-4-hydroxybenzylidenecyanoacetate 5.4 g of 3,5-di-tertiary-butyl-4-hydroxybenzaldehyde were dissolved in 50 ml of toluene. 5.9 g of 4-tertiary-butylcyclohexyl cyanoacetate, 0.1 g of piperidine and 0.25 g of acetic acid were added. 0.4 g of water was removed azeotropically under reflux. The mixture was washed, dried and concentrated.

Yield: 10.6 g (96%) of crystals

| | | Properties: | | |
|---|---|---|---|---|
| Example | $\lambda_{max}$ [nm] | $E_1^A$ | Solubility | Photostability |
| 1 | 356 | 484 | good | 98% |
| 2 | 357 | 638 | very good | 99% |
| 3 | 355 | 623 | good | 92% |

Comparative Example 1

| $\lambda_{max}$ [nm] | $E_1^A$ | Solubility | Photostability |
|---|---|---|---|
| 342 | 904 | very good | 79% |

Comparative Example 2

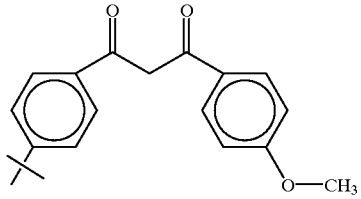

|  | λ_max [nm] | $E_1^A$ | Solubility | Photostability |
|---|---|---|---|---|
| Parsol 1789 | 357 | 638 | good | 55% |

It is evident that the compounds according to the invention display surprising advantages, especially in the important property of photostability, compared with a known compound of similar structure and compared with a licensed commercial product.

Use Examples

Cosmetic compositions in which the compounds according to the invention can be used with particular advantage are indicated below.

General method for producing emulsions for cosmetic purposes:

All the oil-soluble ingredients are heated to 85° C. in a stirred vessel.

When all the ingredients have melted and are in the form of a liquid phase, the aqueous phase is incorporated with homogenization.

While stirring, the emulsion is cooled to about 40° C., perfume is added, and the mixture is then homogenized and cooled to 25° C. while stirring continuously.

Composition for the lip salve
ad 100 Eucerinum anhydricum
10.00 Glycerol
10.00 Titanium dioxide
0.5–10 Compound from Example 1
8.00 Octyl methoxycinnamate
5.00 zinc oxide
4.00 Castor oil
4.00 Pentaeryhrithyl [sic] stearate/caprate/caprylate adipate [sic]
3.00 Glyceryl stearate SE
2.00 Beeswax
2.00 Microcrystalline wax
2.00 Quaternium-18 bentonite
1.50 PEG-45/Dodecyl glycol copolymer Composition for sunblocker with micropigments
ad 100 Water
10.00 Parsol MCX octyl methoxcinnamate [sic]
6.00 PEG-7-hydrogenated castor oil
6.00 Titanium dioxide
0.5–10 Compound from Example 1
5.00 Mineral oil
5.00 Isoamyl p-methoxycinnamate
5.00 Propylene glycol
3.00 Jojoba oil
3.00 4-Methylbenzylidene camphor
2.00 PEG-45/dodecyl glycol copolymer
1.00 Butyl methoxydibenzoylmethane
1.00 Dimethicone
0.50 PEG-40-hydrogenated castor oil
0.50 Tocopheryl acetate
0.50 Phenoxyethanol
0.20 EDTA Non-greasy gel
ad 100 Water
8.00 Octyl methoxycinnamate
7.00 Titanium dioxide
0.5–10 Compound of Example 2
5.00 Glycerol
5.00 PEG-25 PABA
1.00 4-Methylbenzylidene camphor
0.40 Acrylates C10–C30 alkyl acrylate crosspolymer [sic]
0.30 Imidazolidinyl urea
0.25 Hydroxyethyl cellulose
0.25 Sodium methylparaben
0.20 Disodium EDTA
0.15 Fragrance
0.15 Sodium propylparaben
0.10 Sodium hydroxide Sun cream (SPF 20)
ad 100 Water
8.00 Octyl methoxycinnamate
8.00 Titanium dioxide
6.00 PEG-7-hydrogenated castor oil
0.5–10 Compound of Example 2
6.00 Mineral oil
5.00 Zinc oxide
5.00 Isopropyl palmitate
5.00 Imidazolidinyl urea
3.00 Jojoba oil
2.00 PEG-45/dodecyl glycol copolymer
1.00 4-Methylbenzylidene camphor
0.60 Magnesium stearate
0.50 Tocopheryl acetate
0.25 Methylparaben
0.20 Disodium EDTA
0.15 Propylparaben Sun cream, water-resistant
ad 100 Water
8.00 octyl methoxycinnamate
5.00 PEG-7-hydrogenated castor oil
5.00 Propylene glycol
4.00 Isopropyl palmitate
4.00 Caprylic/capric triglyceride
0.5–10 Compound of Example 2
4.00 Glycerol
3.00 Jojoba oil
2.00 4-Methylbenzylidene camphor
2.00 Titanium dioxide
1.50 PEG-45/dodecyl glycol copolymer 1.50 Dimethicone
0.70 Magnesium sulfate
0.50 Magnesium stearate
0.15 Fragrance Sun lotion (SPF 6)

ad 100 Water
10.00 Mineral oil
6.00 PEG-7-hydrogenated castor oil
5.00 Isopropyl palmitate
3.50 octyl methoxycinnamate
0.5–10 Compound of Example 2
3.00 Caprylic/capric triglyceride
3.00 Jojoba oil
2.00 PEG-45/dodecyl glycol copolymer
0.70 Magnesium sulfate
0.60 Magnesium stearate
0.50 Tocopheryl acetate
0.30 Glycerol
0.25 Methylparaben
0.15 Propylparaben
0.05 Tocopherol

We claim:

1. A compound of the formula I

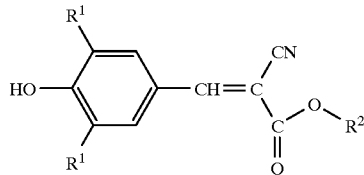

where $R^1$ is i-propyl, i-butyl or t-butyl, $R^2$ is alkyl with 6–14 carbon atoms,

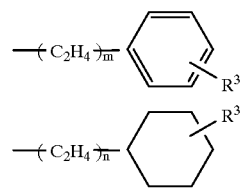

with $R^3$=H or $C_1$–$C_4$-alkyl and m, n=0 or 1.

2. A compound of the formula I as claimed in claim 1, where $R^1$ is t-butyl and $R^2$ is a branched alkyl radical with 8–12 carbon atoms, —$C_2H_4$—$C_6H_5$ or

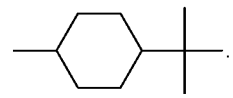

3. A compound of the formula I as claimed in claim 1, where $R^1$ is t-butyl and $R^2$ is

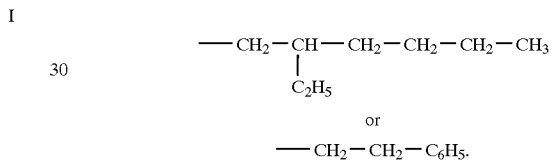

4. A cosmetic composition which comprises as sunscreen agent a compound as claimed in claim 1 alone or together with other UV-A or UV-B filters.

* * * * *